(12) United States Patent
Grandas Sagarra et al.

(10) Patent No.: US 8,816,062 B2
(45) Date of Patent: Aug. 26, 2014

(54) MALEIMIDE-FURANYL COMPOUNDS THAT CAN BE USED IN A GENERAL METHOD FOR PREPARING MALEIMIDE-OLIGONUCLEOTIDE DERIVATIVES

(75) Inventors: Ana María Grandas Sagarra, Barcelona (ES); Albert Sánchez González, Mataró (ES); Enrique Pedroso Muller, Barcelona (ES)

(73) Assignee: Universitat de Barcelona, Barcelona (ES)

( * ) Notice: Subject to any disclaimer, the term of this patent is extended or adjusted under 35 U.S.C. 154(b) by 36 days.

(21) Appl. No.: 13/816,841

(22) PCT Filed: May 2, 2011

(86) PCT No.: PCT/ES2011/070311
§ 371 (c)(1),
(2), (4) Date: Mar. 8, 2013

(87) PCT Pub. No.: WO2012/025646
PCT Pub. Date: Mar. 1, 2012

(65) Prior Publication Data
US 2013/0158248 A1      Jun. 20, 2013

(30) Foreign Application Priority Data

Aug. 27, 2010   (ES) .................................. 201031290

(51) Int. Cl.
| | | |
|---|---|---|
| C07H 21/00 | (2006.01) | |
| C07F 9/6561 | (2006.01) | |
| C07H 1/00 | (2006.01) | |
| C07D 491/08 | (2006.01) | |

(52) U.S. Cl.
CPC ................ C07H 1/00 (2013.01); C07F 9/6561 (2013.01); C07D 491/08 (2013.01); C07H 21/00 (2013.01)
USPC ....... 536/25.3; 536/23.1; 536/25.31; 536/124

(58) Field of Classification Search
None
See application file for complete search history.

(56) References Cited

PUBLICATIONS

Cobb, A. "Recent highlights in modified oligonucleotide chemistry", Organic & Biomolecular Chemistry. vol. 5, pp. 3260-3275 (2007).
Cunliffe, et al. "Synthetic and biological polymers-merging the interface", European Polymer Journal. vol. 40, pp. 5-25 (2004).
Dispinar et al. "A Diels-Alder/Retro Diels-Alder Strategy to Synthesize Polymers Bearing Maleimide Side Chains", Journals of Polymer Science: Part A: Polymer Chemistry. vol. 45, pp. 4545-4551 (2007).
Gauthier, M. and Harm-Anton, K. "Peptide/protein-polymer conjugates: synthetic strategies and design concepts", Chem. Comm. pp. 2591-2611 (2008).
Harrison, J. and Balasubramanian, S. "Synthesis and hybridization analysis of a small library of peptide-oligonucleotide conjugates", Nucleic Acids Research, vol. 26, No. 13, pp. 3136-3145 (1998).
Herdewijn, P. "Review: Heterocyclic Modifications of Oligonucleotides and Antisense Technology", Antisense & Nucleic Acid Drug Development, vol. 10, pp. 297-310 (2000).
International Search Report corresponding to International Patent Application No. PCT/ES2011/070311 dated Sep. 30, 2011.
Latham-Timmons et al. "Novel Method for the Covalent Immobilization of Oligonucleotides via Diels-Alder Bioconjugation", Nucleosides, Nucleotides & Nucleic Acids, vol. 22, Nos. 5-8, pp. 1495-1497 (2003).
Lönnberg, H. "Solid-Phase Synthesis of Oligonucleotide Conjugates Useful for Delivery and Targeting of Potential Nucleic Acid Therapeutics", Bioconjugate Chemistry, vol. 20, No. 6, pp. 1065-1094 (2009).
Maynard et al. "Synthesis of Norbornenyl Polymers with Bioactive Oligopeptides by Ring-Opening Metathesis Polymerization", Macromolecules, vol. 33, pp. 6239-6248 (2000).
Montalbetti, C. and Falque, V. "Amide bond formation and peptide coupling", Tetrahedron, vol. 61, pp. 10827-10852 (2005).
Singh et al. "Chemical Strategies for Oligonucleotide-Conjugates Synthesis", Current Organic Chemistry, vol. 12, pp. 263-290 (2008).
Steven, V. and Graham, D. "Oligonucleotide conjugation to a cell-penetrating (TAT) peptide by Diels-Alder cycloaddition", Organic and Biomolecular Chemistry, vol. 6, pp. 3781-3787 (2008).
Venkatesan et al. "Novel Phosphoramidite Building Blocks in Synthesis and Applications Toward Modified Oligonucleotides", Current Medicinal Chemistry, vol. 10, pp. 1973-1991 (2003).
Zanta et al. "Gene delivery: A single nuclear localization signal peptide is sufficient to carry DNA to the cell nucleus", PNAS, vol. 96, pp. 91-96 (1999).

*Primary Examiner* — Patrick Lewis
(74) *Attorney, Agent, or Firm* — Jenkins, Wilson, Taylor & Hunt, P.A.

(57) ABSTRACT

The compounds of formula (I) substantially in exo form or salts thereof, wherein: X is a biradical selected from —$(CH_2)_n$—*, —$(CH_2CH_2O)_nCH_2CH_2$—*, methylcyclohexyl and methylphenyl; n is an integer ranging between 1 and 30; Y is a radical selected from —COOH, a substituted phosphoramidite radical and N-hydroxysuccinimide ester (or other active ester) of carboxylic acid; and * represents the place through which X binds to Y, are useful in a general process for solid-phase preparation of maleimide-oligonucleotide derivatives.

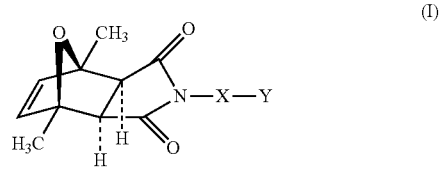

(I)

19 Claims, No Drawings

MALEIMIDE-FURANYL COMPOUNDS THAT CAN BE USED IN A GENERAL METHOD FOR PREPARING MALEIMIDE-OLIGONUCLEOTIDE DERIVATIVES

CROSS-REFERENCE TO RELATED APPLICATIONS

This application is filed under the provisions of 35 U.S.C. §371 and claims the priority of International Patent Application No. PCT/ES2011/070311 filed on May 2, 2011, and of Spanish Patent Application No. P201031290 filed on Aug. 27, 2010. The disclosures of the foregoing international patent application and Spanish patent application are hereby incorporated by reference herein in their respective entireties.

The present invention relates to the field of biotechnology and, particularly, nanotechnology, molecular biology and gene therapy. Namely, the present invention relates to furanyl-maleimide compounds useful as intermediates in a general process for solid-phase preparation of maleimide-oligonucleotide derivatives.

BACKGROUND ART

At present there is a great interest in identifying and developing oligonucleotides which are useful in therapy and diagnostics. The use of oligonucleotides in gene therapy aims the inactivation of the genes involved in the process of a disease. There are several strategies of treatments with oligonucleotides.

Antisense therapy uses oligonucleotides with the sequence complementary to the target gene mRNA, which activates a gene silencing mechanism. It can also be used for altering the transcription of the defective gene by modifying, for example, its introns and exons editing pattern.

iRNA small molecules are also used for activating a gene silencing mechanism similar to that of the antisense therapy.

Another possibility is to use oligodeoxyribonucleotides as a decoy for the factors required in the activation of target genes transcription. Transcription factors are bound to the decoys instead of the promoter of the defective gene, which reduces the expression of the target genes. Moreover, single stranded DNA oligonucleotides have been used for directing the shift of one single base inside the sequence of a mutant gene.

On the other hand, nucleic acid fragments with a suitable label (such as DNA probes) are used in diagnostic for the specific hybridization to a nucleic acid to be detected. The specific sequence of the new double strand is visualized with the aid of the label. Thus, genetic, carcinogenic, viral, or diseases caused by other pathogen agents can be detected.

For the applications mentioned above, there are several limitations associated with the targeting to the specific cell, transport across the cell membrane and oligonucleotide stability. In this way, when the oligonucleotide is administered with a therapeutic or diagnostic purpose, sometimes the result obtained is much lower than expected, since it either does not reach the target cell, or it is not able to pass through the membrane, or it breaks down.

In recent years protocols have been developed with the purpose of overcoming such limitations. These protocols are based on conjugating the oligonucleotide to a molecule which targets, specifically, the oligonucleotide to the target cell, which facilitates the transport across the cell membrane or which stabilizes the oligonucleotide. Examples of molecules that can be used with this purpose are, among others, cell penetrating peptides, lipids or polyamines (cf. H. Lönnberg, "Solid-phase synthesis of oligonucleotide conjugates useful for delivery and targeting of potential nucleic acids therapeutics", *Bioconjugate Chem.* 2009, vol. 20, pp. 1065-1094; Y. Singh et al., "Chemical strategies for oligonucleotide-conjugates synthesis", *Curr. Org. Chem.* 2008, vol. 12, pp. 263-290). Said molecules as well as the labels that can be incorporated into an oligonucleotide are referred to, hereinafter, as "agents".

Numerous protocols by means of which oligonucleotides are conjugated to agents of the type mentioned above are known in the state of the art. In most of these protocols, one of the steps consists of derivatizing the oligonucleotide with a functional group. This derivatization step is needed for being able to generate, in subsequent steps, the oligonucleotide-agent conjugate. In this derivatization step maleimide may be used as a functional group, thus obtaining maleimide-oligonucleotide derivatives. Maleimide derivatization allows the subsequent conjugation of any agent including a nucleophilic group, such as a thiol, or a diene.

To date, the processes disclosed in the state of the art for preparing maleimide-oligonucleotide derivatives take place in solution (cf. Harrison G. H. et al., "Synthesis and hybridization analysis of a small library of peptide-oligonucleotide conjugates", *Nucleic Acids Res.* 1998, vol. 26, pp. 3136-3145; Zanta M. A. et al., "Gene delivery: A single nuclear localization signal peptide is sufficient to carry DNA to the cell nucleus", *Proc. Natl. Acad. Sci.* 1999, vol. 96, pp. 91-96). The processes described for obtaining maleimide-oligonucleotide derivatives show regioselectivity problems due to the fact that they are performed in solution. This negatively affects the purity of the resulting maleimide-oligonucleotide derivative and, in turn, the yield of such processes, since the amount of the derivative finally obtained is reduced as being necessary subsequent steps for its purification. The fact that these processes result in derivatives with low yield and purity affects the subsequent steps, wherein the oligonucleotide, functionalized with the maleimide, is conjugated to the agent of interest (peptide, protein, etc.) in such a way that the oligonucleotide has the desired therapeutic or diagnostic effect. Starting from a small amount of the maleimide-oligonucleotide derivative, a much lower final amount of the oligonucleotide with therapeutic or diagnostic activity to that initially expected is obtained.

Therefore, there is a need for providing processes which allow to obtain maleimide-oligonucleotide derivatives with suitable yield and purity.

SUMMARY OF THE INVENTION

The inventors of the present invention have developed a general process for preparing maleimide-oligonucleotide derivatives in solid-phase which is regioselective. This process comprises, in a first step, coupling a maleimide group to an oligonucleotide of interest (having an intended nanotechnologic, diagnostic or therapeutic application), which is immobilized on a solid support. The inventors have confirmed that when the maleimide group is protected by a furanyl portion, thus forming a new furanyl-maleimide compound, the coupling step is regioselective. Consequently, the general process is automatable, proceeds with high yields and allows to obtain, at the end of the process, a high purity maleimide-oligonucleotide derivative.

A second step of the general process for preparing maleimide-oligonucleotide derivatives of the invention is the release of the oligonucleotide derivative from the support. In this regard, the inventors have found that the furanyl-maleimide compound has to be substantially in the exo configuration since, unlike the endo isomer, the exo isomer is stable under the conditions in which the oligonucleotide is released from the support.

Additionally, the inventors of the present invention have found that using the furanyl-maleimide compound of the invention, which is characterized by comprising methyl groups in positions 2 and 5 of the furanyl portion, the retro-Diels-Alder type reaction may be carried out under milder conditions. This reaction is the last step of the general process of the invention and is carried out in order to finally obtain the maleimide-oligonucleotide derivative of interest.

Due to the foregoing, the furanyl-maleimide compound designed by the inventors of the present invention is a key intermediate in the general process for the invention.

Thus, a first aspect of the present invention relates to a compound of formula (I) substantially in exo configuration, or a salt thereof:

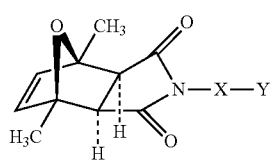
(I)

wherein:
X is a biradical selected from the group consisting of:

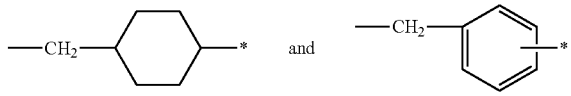

n is an integer ranging between 1 and 30; * representing the place through which X binds to Y; Y is a radical selected from the group consisting of:

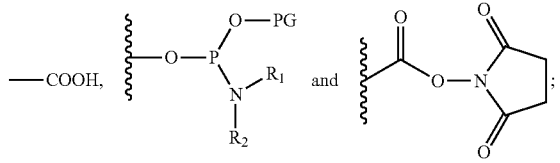

the wavy line representing the place through which Y binds to X; PG is a phosphate protecting group; and $R_1$ and $R_2$ are the same or different to each other and are selected from a $C_1$-$C_{10}$ alkyl radical and a morpholine radical.

As it has been stated above, the general process for preparing the maleimide-oligonucleotide derivatives of the invention is regioselective. This regioselectivity is due, on one hand, to the fact that the maleimide portion is protected by the furanyl portion and, on the other hand, to the fact that the derivatization process is carried out in solid phase.

The compound of formula (I) according to the first aspect of the invention is characterized by having the maleimide portion protected with a furanyl portion. In this way, when the compound of formula (I) reacts with the oligonucleotide (with the purpose of derivatizing it), the reaction takes place through a single point in the maleimide portion (i.e., through the Y radical of the compound of formula (I)), thus avoiding secondary reactions due to the existence of reactivity in other positions of the maleimide portion.

Furthermore, the fact that the oligonucleotide is immobilized on the support assists the derivatization to take place through the desired point of the oligonucleotide. Regioselectivity of the derivatization step may be improved if the oligonucleotide, which is immobilized on the solid support, has the reactive groups (i.e., exocyclic amino, phosphates, and OH groups of the bases) blocked, except the reactive group of the oligonucleotide through which the derivatization reaction with the compound of formula (I) is intended to take place. Protecting groups well-known in the state of the art can be used for blocking the exocyclic amino groups, phosphate groups and hydroxyl groups.

In a second aspect, the present invention relates to a process for preparing the compound of formula (I) defined in the first aspect of the invention, wherein Y is —COOH, comprising the steps of: (a) carrying out a Diels-Alder reaction between a compound of formula (II) and a compound of formula (III),

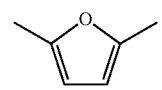
(II)

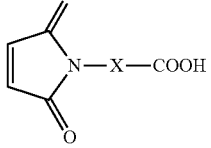
(III)

wherein X is as defined above, and (b) carrying out a treatment of the compound obtained in step (a) with a nucleophilic base for isolating the compound of formula (I).

In a third aspect, the present invention relates to a process for preparing the compound of formula (I) defined in the first aspect of the invention, wherein Y is

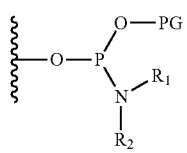

wherein the wavy line, PG, $R_1$ and $R_2$ are as defined above, comprising the reaction of a compound of formula (IV) with a compound of formula (V):

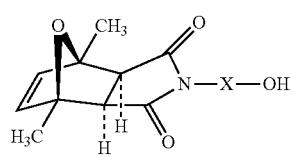
(IV)

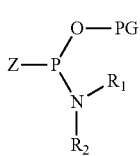

(V)

in an aprotic solvent and under anhydrous conditions, wherein Z is selected from halogen and diisopropylamine, and X is as defined above.

In a fourth aspect, the present invention relates to a process for solid-phase preparation of a maleimide-oligonucleotide derivative of formula (VI), (VI)

wherein X is as defined in the first aspect of the invention, and Y' is selected from wherein the wavy line represents the place through which Y' binds to X, # represents the place through which Y' binds to the oligonucleotide and PG is as defined above; the process comprising the following steps: (a) coupling the compound of formula (I) of the first aspect of the invention to an oligonucleotide that is immobilized on a solid support, in order to obtain the compound of formula (VII)

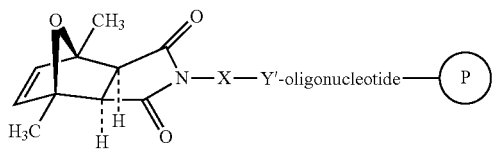

(VII)

wherein P is the solid support, (b) releasing the compound of formula (VII), resulting from step (a), from the solid support to give rise to the compound of formula (VIII);

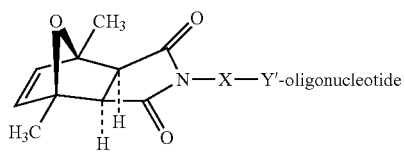

(VIII)

and (c) subjecting the compound of formula (VIII) to a retro-Diels-Alder reaction, such that the derivative of formula (VI) is obtained.

As stated above, the compound of formula (I) and the fact that the coupling to the oligonucleotide takes place in a solid phase confer regioselectivity to the preparation process of the fourth aspect of the invention.

The compound of formula (I) of the invention, depending on the spatial arrangement of its atoms, may adopt an exo or endo configuration. According to the present invention, the compound of formula (I) is found substantially in an exo configuration, which means that it has a percentage of exo isomer equal to or greater than 95%, more preferably equal to or greater than 98%.

The inventors have found that the compound of general formula (I) is stable under the conditions necessary for obtaining the compound (VIII) from the compound (VII). This stability is conferred by the fact that the compound of the invention is substantially in exo configuration. As it is illustrated below, when using ammonia, which is a frequently used reactive for releasing an oligonucleotide from a solid support, it is observed that if a mixture of exo/endo product is used, the recovered product is the one corresponding to the exo adduct, while the endo form breaks down resulting in undesired secondary products. The experimental results obtained allow to conclude that using a compound of formula (I), which is found substantially in exo configuration, a purer compound (VIII) is obtained, since the by-products associated with the degradation of the endo isomer are minimized, and the final yield of the maleimide-oligonucleotide derivative is also higher.

On the other hand, the inventors have confirmed that the fact that the furanyl portion is substituted in positions 2 and 5 with methyl groups allows to carry out the retro-Diels-Alder-type reaction of step (c) under milder conditions. Being able to work under milder conditions minimizes the risk of degradation of the oligonucleotide, which, in turn, contributes to a higher yield of the process.

As it has already been explained above, the production of maleimide-oligonucleotide derivatives is an intermediate step necessary for the oligonucleotide to end up conjugating to the agent which confers cell specificity, stability, or the ability of being transported across the cell membrane (cf. Lönnberg H. et al., supra).

The fact that the maleimide-oligonucleotide derivative of formula (VI) of the present invention is obtained in a regioselective manner and with suitable yield and purity positively affects the subsequent generation of the oligonucleotide-agent conjugates (which are the ones having the intended nanotechnologic, therapeutic or diagnostic application). The purer the maleimide-oligonucleotide derivative, less by-products will be obtained during the conjugation of the agent to the derivative, which positively affects the final yield of the oligonucleotide-agent product since additional purification steps will not be needed.

In a fifth aspect, the present invention relates to a compound of formula (VII)

(VII)

wherein X, Y' and P are as defined above.

In a sixth aspect, the present invention relates to a compound of formula (VIII):

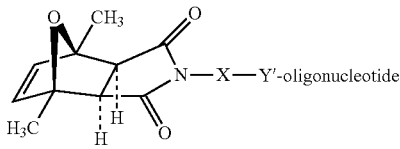

(VIII)

wherein X and Y' are as defined above.

DESCRIPTION OF PARTICULAR EMBODIMENTS

According to the above, in a first aspect the invention relates to a compound of general formula (I) substantially in exo configuration, or a salt thereof. Preferably, $R_1$ and $R_2$ are the same.

The salt of a compound of formula (I) is obtained in the case that Y is —COOH. Processes for preparing carboxylic acid salts are general knowledge for those skilled in the art.

In a preferred embodiment of the first aspect of the invention, $R_1$ and $R_2$ are $C_1$-$C_{10}$ alkyl radicals. Preferably, $R_1$ and $R_2$ are isopropyl.

The phosphate protecting group (PG) may be any of those known in the state of the art (cf. Beaucage S. L. "Oligodeoxyribonucleotides synthesis. Phosphoramidite approach", Chapter 3, "Methods in Molecular Biology", volume 20, "Protocols for oligonucleotides and analogues", Ed. Agrawal S., Humana Press, 1993, pp. 41 and 43). In a preferred embodiment of the first aspect of the invention, the phosphate protecting group is selected from the group consisting of —CH$_2$CH$_2$CN, methyl, 2-cyano-1,1-dimethylethyl and p-nitrophenylethyl.

In another preferred embodiment of the first aspect of the invention, X is —(CH$_2$)$_n$—* or —(CH$_2$CH$_2$O)$_n$CH$_2$CH$_2$—*, * having the same meaning as in the first aspect of the invention. Preferably, n ranges from 1-20, more preferably from 1-10.

In another preferred embodiment of the first aspect of the invention, Y is —COOH or

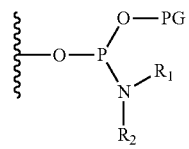

the wavy line, PG, $R_1$ and $R_2$ having the same meaning as in the first aspect of the invention.

In yet another preferred embodiment of the first aspect of the invention, the compound is selected from those of formulae (Ia) and (Ib).

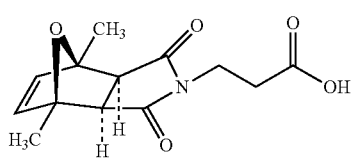

(Ia)

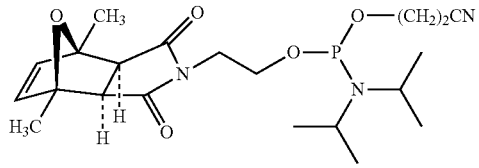

(Ib)

In a second aspect, the present invention provides a process for preparing a compound of formula (I) wherein Y is —COOH.

In a preferred embodiment of the second aspect of the invention, the step (b) of treatment with the nucleophilic base comprises the substeps: (b$_1$) contacting the compound obtained in step (a) with a nucleophilic base at room temperature; (b$_2$) removing the base; (b$_3$) acidifying the resulting medium to a pH equal to or less than 3; and (b$_4$) isolating the resulting product. Preferably, the resulting medium is acidified to a pH of 1-2. Preferably, the nucleophilic base is selected from ammonia, a primary amine and a secondary amine. More preferably, the nucleophilic base from step (b) is ammonia.

In another preferred embodiment of the second aspect of the invention, step (b) of treatment with a nucleophilic base of the process can be repeated as many times as necessary for achieving the intended exo isomer ratio.

In a third aspect, the present invention provides a process for preparing a compound of formula (I) wherein Y is

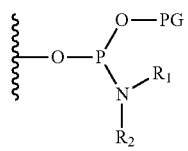

wherein the wavy line, PG, $R_1$ and $R_2$ are as defined in the first aspect of the invention.

In a preferred embodiment of the third aspect of the invention, Z is chlorine or diisopropylamine.

In another embodiment of the third aspect of the invention, when Z is chlorine, the reaction between the compound of formula (IV) and (V) takes place in the presence of a tertiary amine.

In another embodiment of the third aspect of the invention, when Z is diisopropylamine, the reaction between the compound of formula (IV) and (V) takes place in the presence of a tetrazole.

Compounds of formula (I) wherein Y is

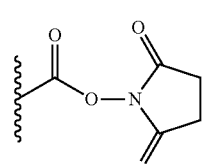

the wavy line having the same meaning as in the first aspect of the invention, may be obtained according to the following reaction scheme.

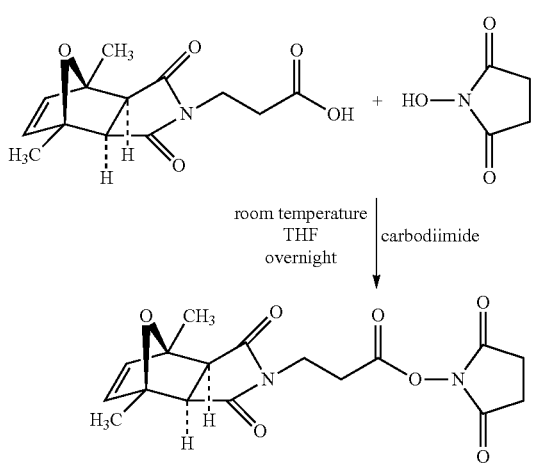 [SMILES: C[C@]12C=C[C@](C)(O1)[C@@H]1C(=O)N(CCC(=O)O)C(=O)[C@@H]12 ; O=C1CCC(=O)N1O ; C[C@]12C=C[C@](C)(O1)[C@@H]1C(=O)N(CCC(=O)ON3C(=O)CCC3=O)C(=O)[C@@H]12]

In a fourth aspect, the invention provides a process for preparing a maleimide-oligonucleotide of formula (VI), according to the stated above.

The solid support for carrying out the process may be any of those known in the state of the art which is suitable for oligonucleotides assembly. By way of an illustrative and not limitative example, the support can be made of silicates, silica, polystyrene or miscellaneous polymer networks. Among the first, controlled pore size glass ("CPG") supports which have the additional advantages of mechanical strength, accessibility of functional groups irrespective of the choice of the organic solvent and possibility of varying the porosity of the support should be highlighted.

The oligonucleotide immobilized on the solid support may be anyone of interest for those skilled in the art either for having a nanotechnologic, therapeutic or diagnostic application. Thus, the oligonucleotide immobilized on the solid support can be natural DNA or RNA. Optionally, nucleotides constituting the oligonucleotide may be modified. These modifications can be found in the sugar, base and/or phosphate portion. Processes for carrying out such modifications are well-known in the state of the art. Illustrative and not limitative examples of oligonucleotides with modified sugars are those wherein the sugar has been replaced by a morpholino portion, LNA derivatives ("Locked nucleic acid"), 2'-OMe or 2'-F; illustrative and not limitative examples of modified bases are 5-Me-dC, 5-propynyl-dC, deaza nucleobases, 5-Me-U, 5-Br—U and 2-aminopurine; and illustrative and not limitative examples of modified phosphates are Me-phosphonates, phosphorothioates and phosphoramidates.

Step (a) of the process of the fourth aspect of the invention can be carried out in the presence of any of the coupling agents usually used in peptide synthesis. In a preferred embodiment of the process of the fourth aspect of the invention, step (a) is carried out in the presence of the coupling agent pentafluorophenyl 4-nitrobenzene sulphonate and the catalyst 1-hydroxybenzotriazole.

At the time of carrying out step (a) of the process of the fourth aspect of the invention, the oligonucleotide is immobilized on the solid support by its 3'- or 5'-end. Said oligonucleotide may have been synthesized in situ, following well-established and routine protocols for those skilled in the art, who will be able to determine the suitable reaction conditions (such as protecting groups, activation conditions, etc.) for generating the oligonucleotide of interest (cf. Beaucage S. L. "Oligodeoxyribonucleotides synthesis. Phosphoramidite approach", Chapter 3, Methods in Molecular Biology, volume 20: "Protocols for oligonucleotides and analogues", Ed. Agrawal S., Humana Press 1993, pp. 33-61). An alternative would be to immobilize the oligonucleotide obtained by other means (for example, it may have been isolated from a genomic library) on the support.

When step (a) of the process of the fourth aspect of the invention is performed, the derivatization of the oligonucleotide takes place between the Y radical of the compound of formula (I) of the first aspect of the invention and an oligonucleotide free —OH or —NH$_2$ group.

For obtaining an oligonucleotide with a free —NH$_2$ group, an amino alcohol (anyone of the commercially available) wherein the —NH$_2$ group is protected with a protecting group (for example, monomethoxy trityl (MMT)) and the —OH group is derivatized as a phosphoramidite group, is incorporated into the oligonucleotide, by any of the processes well-known in the state of the art. Next, the protecting group of the amino group is removed, thus the free —NH$_2$ group being able now to react with the Y radical of the compound of formula (I).

Taking into account the meaning of Y, the derivatization that takes place in step (a) can be as follows:
a) when Y is —COOH or

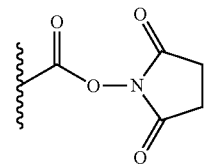 [SMILES: *C(=O)ON1C(=O)CCC1=O]

the derivatization takes place with a free —NH$_2$ group of the oligonucleotide, an amide linkage being generated (cf. Montalbetti C. A. G. N. et al., "Amide bond formation and peptide coupling", Tetrahedron 2005, vol. 61, pp. 10827-10852). In this way, Y, upon derivatization, turns into Y'=—CO—; and
b) when Y is

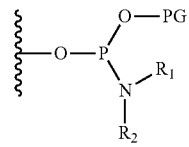

the derivatization takes place with a free —OH group of the oligonucleotide, a phosphotriester group being generated (cf. Beaucage, S. L. et al., "Advances in the synthesis of oligonucleotides by the phosphoramidite approach", Tetrahedron 1992, vol. 48, pp. 2223-2311). In this way, Y, upon derivatization, turns into Y'

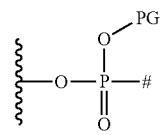

The —OH or —NH$_2$ group through which derivatization takes place can be located in the 5', 3' end or in a non-terminal nucleotide, that is, that it is not occupying the terminal position (5' or 3') in the oligonucleotide.

It is preferable that the oligonucleotide has all the reactive —OH and —NH₂ groups chemically modified, except the —OH or —NH₂ group through which the derivatization reaction of step (a) is desired to take place. Thus, regioselectivity of the step is improved, since the compound of formula (I) will be able to react only with the free —OH/—NH₂ (that is, with the non-chemically modified —OH/—NH₂). Depending on the modification carried out in the nucleotides forming the oligonucleotide, the derivatization with the compound of formula (I) will take place in one position or other.

By way of illustration and without limitation, an oligonucleotide can be synthesized in solid phase using nucleosides presenting a phosphoramidite group. Herefrom, different scenarios could occur depending on where they bear the phosphoramidite group: (a) using 3'-phosphoramidite nucleosides (cf. Beaucage S. L. 1993, supra; Brown T. et al., "Modern machine-aided methods of oligodeoxyribonucleotide synthesis", Chapter 1, "Oligonucleotides and Analogues, A Practical Approach", Ed. Eckstein F., Oxford University Press, 1991, pp. 1-24), derivatization could take place through the 5'-end of the resulting oligonucleotide, which is the one that would remain free; and (b) using 5'-phosphoramidite nucleosides (cf. Beaucage S. L. 1993, supra) derivatization could take place through the 3'-end of the resulting oligonucleotide, which is the one that would remain free.

Oligonucleotides with the maleimide of formula (I) bound to a base or a sugar can be obtained, using for their synthesis nucleoside derivatives with the base or sugar portion suitably modified. There are well-established protocols in the state of the art for modifying the reactive regions of the nucleotides constituting an oligonucleotide (cf. Herdewijn P., "Heterocyclic modifications of oligonucleotides and antisense technology", *Antisense & Nucleic Acid Drug Development* 2000, vol. 10, pp. 297-310; Cobb A. J. A., "Recent highlights in modified oligonucleotide chemistry", *Org. Biomol. Chem.* 2007, vol. 5, pp. 3260-3275; Venkatesan N. et al., "Novel phosphoramidite building blocks in synthesis and applications toward modified oligonucleotides", *Curr. Med. Chem.* 2003, vol. 10, pp. 1973-1991).

Once the compound of formula (VII) is generated (i.e., once the derivatization of the oligonucleotide has taken place), it is released from the support using any of the well-established protocols in the state of the art. Those skilled in the art will be able to choose any of these protocols provided that the reaction conditions used do not break down the compound of formula (VII) generated in step (a). In a preferred embodiment, the compound of formula (VIII) is released from the solid phase support by adding a nucleophilic base. Illustrative and not limitative examples of nucleophilic bases are ammonia, primary amines and secondary amines. Preferably, the nucleophilic base is ammonia.

The conditions under which both the Diels-Alder of the process of the second aspect of the invention, and the retro-Diels-Alder of the process of the fourth aspect of the invention take place are well-known by those skilled in the art. Preferably, the retro-Diels-Alder reaction is carried out with microwaves at a temperature comprised between 80-100° C.

Alternatively, the retro-Diels-Alder reaction used to obtain the maleimide-oligonucleotide derivative of formula (VI) from compound of formula (VIII) according to step (c) of the previously described procedure for the preparation of maleimide-oligonucleotide derivative of formula (VI), may be carried out by adding an aromatic hydrocarbon (C₆-C₈) to the product resulting from step (b), dry (this product may be dried by coevaporation with the same aromatic hydrocarbon), and heating at a temperature ranging between 80 and 100° C. Preferably the aromatic hydrocarbon is toluene. Preferably, the reaction is carried out at about 90° C. In general, reaction time varies between 2 and 5 hours.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1

Preparation of 3-(1,7-dimethyl-3,5-dioxo-10-oxa-4-aza-tricycle[5.2.1.0²·⁶]dec-8-en-4-yl)propanoic acid (Ia)

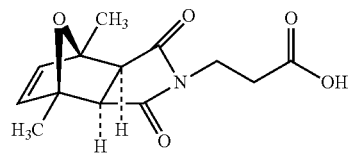

100 mg (0.59 mmol) of 3-maleimide propionic acid were weighed and dissolved in 2 ml of acetonitrile. Next, 400 µl of 2,5-dimethylfuran (3.72 mmol) were added and the pool was heated at 60° C. with constant stirring for 6 h. After this time the solvent was removed under reduced pressure, obtaining the compound Ia as an ochre oil in a quantitative manner. The product was characterized by ESI-MS (negative mode) and ¹H-RMN. The ratio of exo/endo diastereomers of the Diels-Alder adduct formed, determined from the integration of the signal areas of the olefinic CH (δ 6.30 ppm for the exo adduct and δ 6.19 ppm for the endo adduct) at the ¹H-RMN spectrum, was: 78:22. For the integration of the areas the software MestRe-C was used.

¹H-RMN (CDCl₃, 400 MHz): exo adduct: δ 6.30 (s, 2H), 3.79 (t, J=7.3 Hz, 2H) 2.83 (s, 2H), 2.67 (t, J=7.3 Hz, 2H), 1.70 (s, 6H) ppm; endo adduct: δ 6.19 (s, 2H), 3.64 (t, J=7.3 Hz, 2H) 3.22 (s, 2H), 2.54 (t, J=7.3 Hz, 2H), 1.78 (s, 6H) ppm. ESI-MS (negative mode) m/z 263.83 [M−H]-(M calc: 265.10).

Next, 100 mg (0.38 mmol) of the Ia acid exo/endo mixture 78:22 were weighed and dissolved in 4 ml of 32% (44 mmol) ammonia concentrated aqueous solution. The reaction mixture was kept at room temperature and under stirring overnight. Subsequently, ammonia was removed under reduced pressure and the obtained aqueous solution was acidified with trifluoroacetic acid to pH 1-2. Immediately after the aqueous solution was extracted with dichloromethane (3×10 ml). The organic phase was dried with anhydrous magnesium sulphate. Then the solid was filtered and the solvent was removed to dryness. Ia acid was isolated with a 90% yield. The product was characterized by ¹H-RMN. The obtained spectrum was the same as that stated in the previous paragraph, while peak areas were different. Next, the ratio of the diastereomers of the product was determined by the integration of the signal areas of the olefinic CH in the ¹H-RMN spectrum (δ 6.30 ppm for the exo adduct and δ 6.19 ppm for the endo adduct) using MestRe-C software. Thus, the exo/endo ratio was determined to be 98:2.

Example 2

Preparation of 3-(1,7-dimethyl-3,5-dioxo-10-oxa-4-aza-tricycle[5.2.1.0$^{2.6}$]dec-8-en-4-yl)propanoyl-NH—(CH$_2$)$_6$—O—(PO)(OCNE)-$^5$O-[dT$_{10}$ protected]-succinyl-CPG

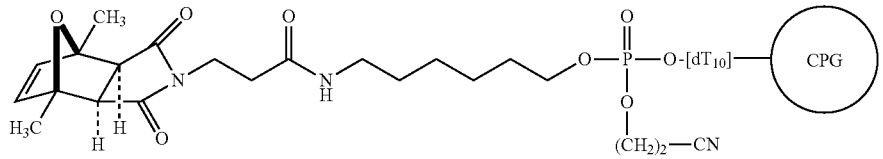

The synthesis of the oligonucleotide strand modified in its 5' end with an amino group (protected) was carried out under standard conditions following the phosphite-triester process, in an ABI 3400 synthesizer and at a 1 μmol scale. 5'-DMT-dT (0.1 M) and MMT-amino-C6 (0.15 M) commercial phosphoramidites were used, as well as the standard CPG solid support functionalized with the first nucleoside.

The monomethoxytrityl (MMT) protecting group of the amino group was removed by successive treatments with detrityling solution until disappearance of the deep yellow color characteristic of the MMT cation. Next, the resin was washed with dichloromethane.

For the coupling of the Ia acid to 0.5 μmol of oligonucleotidyl-resin, 1.7 mg (6.4 μmol) of acid 1, 2.7 mg (7.3 μmol) of the coupling agent PFNB (pentafluorophenyl 4-nitrobenzenesulphonate) and 1.0 mg (7.4 μmol) of 1-hydroxybenzotriazole (HOBt) were weighed. The pool was dissolved in 100 μl of 0.8 M LiCl solution in N-methylpyrrolidinone/N,N-dimethylformamide 1:1 (v/v). Immediately after, 5.0 μL of N,N-diisopropylethylamine (DIEA) (29.4 μmol) were added to the solution and the mixture was kept under stirring and at room temperature for 15 minutes to ensure a good activation of the Ia acid. After this time, it was added to the reactor containing the resin. The resin was left tightly covered for preventing the loss of reactives and under constant stirring for 6 h. After this time it was filtered and the excess of reactives was removed by washing with N,N-dimethylformamide (3×5 ml), dichloromethane (3×5 ml) and methanol (3×5 ml). The resin was dried with argon stream.

Example 3

Preparation of 3-(1,7-dimethyl-3,5-dioxo-10-oxa-4-aza-tricycle[5.2.1.0$^{2.6}$]dec-8-en-4-yl)propanoyl-NH—(CH$_2$)$_6$—O—(PO)—$^5$O-dT$_{10}$

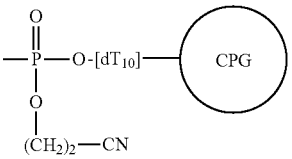

0.3 μmol of 3-(1,7-dimethyl-3,5-dioxo-10-oxa-4-aza-tricycle[5.2.1.0$^{2.6}$]dec-8-en-4-yl)propanoyl-NH—(CH$_2$)$_6$—

O—(PO)(OCNE)-$^5$'O-[dT$_{10}$ protected]-succinyl-CPG were introduced in a screw cap vial and 300 μL of ammonia concentrated aqueous solution (32%) were added. After 90 min of reaction at room temperature, it was filtered, the resin was washed with water, and the ammonia was removed from the filtrate under reduced pressure. The resulting aqueous solution was frozen and lyophilized.

When the experiment described in example 2 was carried out with a mixture of the two Ia diastereomers at an exo/endo ratio of 78:22, the reverse phase HPLC (C18) analysis of the deblocking crude showed two peaks with retention times of 15.1 min (23%) and 17.8 min (77%), respectively (analysis conditions: 5 to 60% of B in 30 min, A: TEAA 0.05 M (TEAA=triethylammonium acetate) and B: acetonitrile/water 1:1, v/v). Both products were collected and analyzed by ESI-MS (negative mode). The 17.8 min (77%) retention time product corresponded to the desired oligonucleotide (m/z 3406, M calc 3407), and the 15.1 min (23%) retention time corresponded to the same oligonucleotide with the imide hydrolyzed (m/z 3424, M calc. 3425).

On the other hand, when the experiment described in example 2 is carried out with Ia substantially in exo configuration (exo) the reverse phase HPLC analysis of the deblocking crude shows that the desired product (retention time 17.8 min) is found at 97%. Results indicate that only the exo adduct remains stable to the ammonia treatment, but not the endo adduct. Consequently, the exo adduct of the oligonucleotide modified with the protected maleimide is obtained.

The product was purified by semi-preparative HPLC (Phenomenex column (C18), 250×10 mm, 10 μm, analysis conditions: 5 to 60% of B in 30 min, A: TEAA 0.05 M and B: acetonitrile/water 1:1, v/v). The 5'-modified oligonucleotide (exo adduct) was obtained, ESI-MS (positive mode): m/z 3405.72 [M+H]$^+$ (M calc 3404.66).

Example 4

Preparation of 5'-maleimide-oliqonucleotide (dT10)

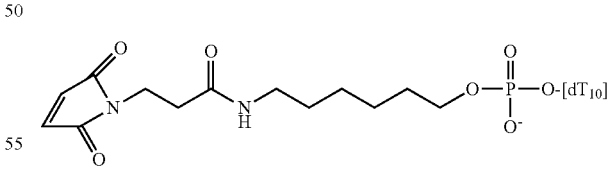

In a microwave vial with a 200-500 μl capacity, 200 μl of a 2.46×10$^{-2}$ mM solution of 3-(1,7-dimethyl-3,5-dioxo-10-oxa-4-aza-tricycle[5.2.1.0$^{2.6}$]dec-8-en-4-yl)propanoyl-NH—(CH$_2$)$_6$—O—(PO$_2^-$)—$^5$O-dT$_{10}$ in methanol/water 1:1 (v/v) were introduced. Next, the solution was subjected to microwave irradiation for 60 min at 90° C.

HPLC analysis of the crude showed two peaks with retention times of 15.9 min (73%) and 17.7 min (27%), respectively (analysis conditions: 5 to 60% of B in 30 min, A: TEAA 0.05 M and B: acetonitrile/water 1:1 v/v). The analysis by ESI-MS (negative mode) of the previous products revealed that the peak with a 15.9 min retention time corresponded to the 5'-terminal functionalized oligonucleotide with a maleimide group (m/z 3309, M calc 3310), and the peak with a 17.8 min retention time corresponded to a starting product wherein the maleimide had not been deprotected.

Example 5

Preparation of [2-(1,7-dimethyl-3,5-dioxo-10-oxa-4-aza-tricycle[5.2.1.0$^{2.6}$]dec-8-en-4-yl)-ethyl](N,N-diisopropyl)(2-cyanoethyl)phosphoramidite (Ib)

a) N-(2-hydroxyethyl)maleimide

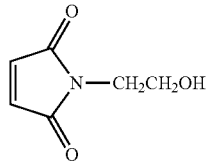

N-(2-hydroxyethyl)maleimide was prepared according to what is described in Heath W. H. et al., "Degradable crosslinkers and strippable imaging materials for step-and-flash imprint lithography", *Macromolecules* 2008, vol. 41, pp. 719-726.

b) 4-(2-hydroxyethyl)-1,7-dimethyl-10-oxa-4-aza-tricycle[5.2.1.0$^{2.6}$]dec-8-en-3,5-dione, exo isomer

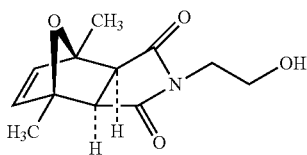 [SMILES: C[C@]12C=C[C@](C)(O1)[C@@H]1C(=O)N(CCO)C(=O)[C@@H]12]

A mixture of N-(2-hydroxyethyl)maleimide (800 mg, 5.67 mmol), 2,5-dimethylfuran (3.2 ml, 30.1 mmol) and acetonitrile (13 ml) was heated at 65° C. overnight under argon atmosphere. After this time, the mixture was allowed to cool to room temperature and evaporated to dryness, affording an oil. The product was characterized by $^1$H-RMN. Next the ratio of the exo/endo diastereomers of the product was determined by the integration of the signal areas of the olefinic CH in the $^1$H-RMN spectrum (δ 6.32 ppm for the exo adduct and δ 6.23 ppm for the endo adduct) using the MestRe-C software. Thus, it was determined that the relative ratio of the exo/endo isomers was 4:1.

$^1$H-RMN (CDCl$_3$, 400 MHz) exo adduct: δ 6.32 (s, 2H), 3.76 (t, J=4.5 Hz, 2H), 3.70 (t, J=4.5 Hz, 2H), 2.87 (s, 2H). 1.71 (s, 6H) ppm; endo adduct: δ 6.23 (s, 2H), 3.74 (t, J=4.5 Hz, 2H), 3.57 (t, J=4.5 Hz, 2H), 3.26 (s, 2H), 1.79 (s, 6H) ppm.

Next, 500 mg of the 4:1 mixture of 2-(2,5-dimethylfuryl-maleimidyl)ethanol exo and endo isomers were treated with 25 ml of an ammonia concentrated aqueous solution (32%) overnight. After this time, the ammonia was removed in the rotary evaporator, the sample being concentrated to a volume of about 5 ml. This aqueous solution was diluted with 20 ml of NaCl saturated aqueous solution and 5 ml of 10% HCl aqueous solution, and was extracted with dichloromethane (4×200 ml). The total of the organic phases was dried over MgSO$_4$ and the solvent was removed in the rotary evaporator. The product was characterized by $^1$H-RMN. The peaks of the obtained spectrum were characteristic of the exo form, thus concluding that the resulting oil (340 mg) contained only the 4-(2-hydroxyethyl)-1,7-dimethyl-10-oxa-4-aza-tricycle [5.2.1.0$^{2.6}$]dec-8-en-3,5-dione exo isomer.

c) [2-(1,7-dimethyl-3,5-dioxo-10-oxa-4-aza-tricycle [5.2.1.0$^{2.6}$]dec-8-en-4-yl)-ethyl](N,N-diisopropyl)(2-cyanoethyl)phosphoramidite (Ib)

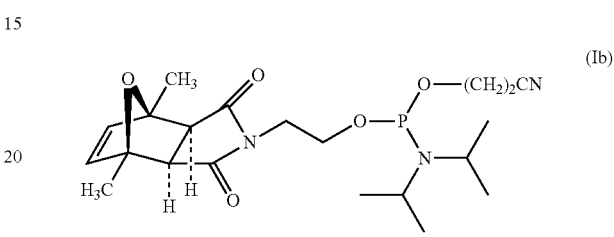

350 mg of the product obtained in the previous section (b) (1.48 mmol) were dried by coevaporation with anhydrous acetonitrile (2×). After adding anhydrous dichloromethane (1 ml), triethylamine (1 ml, 7.17 mmol) and (2-cyanoetoxy) chloro(diisopropylamine)phosphine (360 µl, 1.55 mmol), the mixture was allowed to react at room temperature and under argon atmosphere for 1 h. After this time, 10 ml of dichloromethane were added and extractions with 5% NaHCO$_3$ aqueous solution (2×25 ml) and NaCl saturated aqueous solution (1×25 ml) were carried out. The organic phase was dried over MgSO$_4$ and the solvent was removed in the rotary evaporator. $^{31}$P-RMN analysis of the resulting product showed the expected signal for a phosphoramidite (δ 148 ppm), in addition to small impurities at 14 and 8 ppm. The product was obtained pure ($^{31}$P-RMN: δ 148 ppm) after column chromatography over silica gel, by eluting with dichloromethane and 5% triethylamine.

Example 6

[2-(1,7-dimethyl-3,5-dioxo-10-oxa-4-azatricycle [5.2.1.0$^{2.6}$]dec-8-en-4-yl)-ethyl]-O—PO$_2^-$)—5'O-dT$_{10}$

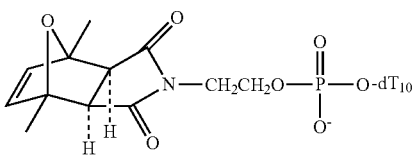

The synthesis of the oligonucleotide strand was carried out under standard conditions following the phosphite triester method, in an ABI 3400 synthesizer and at a 1 µmol scale. 5'-DMT-dT commercial phosphoramidite (0.1 M) and CPG standard solid support functionalized with the first nucleoside were used.

Once the elongation of the oligonucleotide strand was performed, the 5' end protecting dimethoxytrityl was removed, in the same synthesizer, and the Ib phosphoramidite derivative (0.13 M) was incorporated using the same methodology as for the elongation of the oligonucleotide strand (double coupling, 5 min/coupling) described in the previous paragraph.

An aliquot of oligonucleotidyl-resin corresponding to 0.1 µmol of oligonucleotide was introduced into a screw cap vial and treated with 100 µl of ammonia concentrated aqueous solution for 1 h at room temperature, after which the resin was filtered and washed with water. The ammonia was removed from the filtrate under reduced pressure. The resulting aqueous solution was frozen and lyophilized. The analysis by HPLC of the deblocking crude showed a peak practically unique with a retention time of 15.8 min. (99%) (analysis conditions: 5 to 60% of B in 30 min., A: TEAA 0.05 M and B: acetonitrile/water 1:1, v/v). This peak corresponded to the 5'-terminal functionalized oligonucleotide with the maleimide protected in exo configuration.

MALDI TOF-MS (THAP=trihydroxyacetophenone, ammonium citrate, negative mode): m/z 3276.47 (M calc 3277.56).

Example 7

5'Maleimide-oligonucleotide (dT$_{10}$)

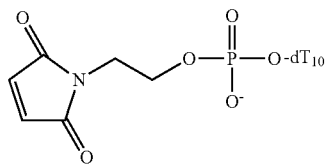 [SMILES: O=C1C=CC(=O)N1CCOP(=O)([O-])O]

A 12.5 µM solution of the resulting product from the treatment with ammonia ([2-(1,7-dimethyl-3,5-dioxo-10-oxa-4-azatricycle[5.2.1.0$^{2.6}$]dec-8-en-4-yl)-ethyl]-O—PO$_2$$^-$)—$^{5'}$O-dT$_{10}$) in MeOH/H$_2$O 1:1 (v/v) (200 µL) was introduced into a microwave vial and irradiated at 90° C. for 90 min. After removing the methanol in the rotatory evaporator, the analysis of the crude was carried out by HPLC. The chromatogram showed, in addition to small impurities, a peak with a 15.8 min (<5%) retention time, corresponding to the starting product, and a majority peak with a retention time of 14.3 min (85%) corresponding to the desired maleimide-oligonucleotide (analysis conditions: 5 to 60% B at 30 min, A: TEAA 0.05 M and B: acetonitrile/water 1:1, v/v). MALDI TOF-MS (THAP, ammonium citrate, negative mode): m/z 3180.46 (M calc 3181.50).

Example 8

Effect of the Presence of Methyl Groups in Position 2 and 5 of the Furanyl Portion in the Compound of Formula (I)

With the purpose of determining whether the presence of methyl groups in the furanyl portion of the compound of formula (I) somehow affected the process for preparing the maleimide-oligonucleotide derivative, the retro-Diels-Alder reaction for compounds (a) and (b) was carried out:

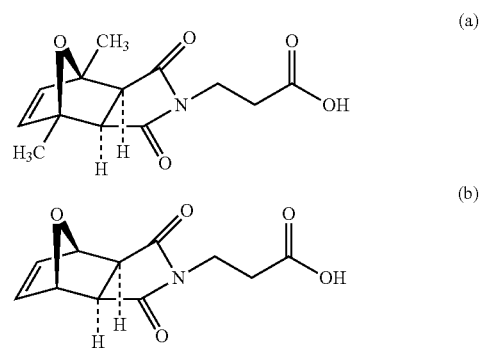

Compound (a) corresponds to an embodiment of the present invention.

Compound (b) is included for comparative purposes.

Each one of the compounds was dissolved in a methanol:water 1:1 (v/v) mixture. Herefrom:
for compound (a) it was determined that irradiating with microwaves at 80° C. for 10 minutes, a 92% of free maleimide portion was achieved; and
for compound (b) it was determined that irradiating with microwaves at 120° C. for 10 minutes, a 96% of free maleimide portion was achieved.

In order to determine the free maleimide ratio, a reverse phase HPLC analysis was carried out:
A: water+0.045% trifluoroacetic acid
B: CH$_3$CN+0.036% trifluoroacetic acid
Gradient: from 0 to 15% of B in 30 minutes The retention time of the product obtained during the retro-Diels-Alder was 10.15 minutes. Then, it was confirmed that said retention time corresponded with that determined in a commercial 3-maleimido-propinoic acid sample.

From the results obtained in this assay, it can be concluded that the presence of methyl groups in the furanyl portion makes the conditions of the retro-Diels-Alder reaction milder in comparison to the conditions necessary for achieving a yield of the same order with a furanyl-maleimide derivative wherein the furanyl portion does not include methyl substituents.

The fact that the retro-Diels-Alder can be carried out under milder conditions has the main advantage of respecting the integrity of the oligonucleotide that is bound to the compound of formula (I) of the first aspect of the invention, thus minimizing the risk of oligonucleotide degradation.

Example 9

[2-(1,7-dimethyl-3,5-dioxo-10-oxa-4-azatricyclo [5.2.1.0$^{2.6}$]dec-8-en-4-yl)-ethyl]-O—PO$_2$$^-$)$^{5'}$—O-oligoncleotide

[2-(1,7-dimethyl-3,5-dioxo-10-oxa-4-azatricyclo [5.2.1.0$^{2.6}$]dec-8-en-4-yl)-ethyl](N,N-diisopropyl)(2-cyanoethyl)phosphoramidite was incorporated onto oligonucleotide-resins using a 5-minute double coupling. The step in which unreacted hydroxyls are capped was omitted to allow coupling to be repeated in case the coupling yield was not good enough. After oxidation, an aliquot of resin-linked, fully protected maleimide-oligonucleotide was treated with concentrated aqueous ammonia at room temperature for 1 h, and, after elimination of ammonia under reduced pressure the crude was analyzed by HPLC (C18). Virtually a single peak or a main important peak was observed in all cases. This compound was collected and characterized by mass spectrometry, and it was found to be the expected oligonucleotide [2-(1,7-dimethyl-3,5-dioxo-10-oxa-4-azatricyclo[5.2.1.0$^{2.6}$] dec-8-en-4-yl)-ethyl]-O—PO$_2^-$)—$^{5'}$O-oligonucleotide.

Using this procedure the following oligonucleotides (in addition to [protected maleimide]-dT$_{10}$, previously described): [protected maleimide]-$^{5'}$dCAGATGTCAC, [protected maleimide]-$^{5'}$dTCTCCCAGCGTGCGCCAT, [protected maleimide]-$^{5'}$dCAGCAGCAGAGTCTTCATCAT, and [protected maleimide]-$^{5'}$U$_{10}$ were obtained from the corresponding starting material. For the first three the ammonia treatment was prolonged for 4 h to ensure nucleobase deprotection. In the case of the oligoribonucleotide (U$_{10}$), an aliquot of the crude (0.1 μmol) obtained after the treatment with ammonia (3 h, room temperature) was taken to dryness and coevaporated with absolute ethanol (3×). DMSO (30 μL) and TEA.3HF (30 μL) was added, and the mixture was left to react for 8 h at room temperature. The reagent removing 2'-OH protecting groups was quenched with isopropyl trimethylsilyl ether (120 μL, 10 min reaction time), and the oligoribonucleotide was precipitated by adding 1 mL of anhydrous ether. The mixture was centrifuged at 1100 rpm for 5 min at 5° C. and ether decanted. Ether addition, centrifugation and decantation were repeated twice. The resulting oligoribonucleotide [protected maleimide]-U$_{10}$ was dried under an Argon stream. Crudes were analyzed by HPLC (C18). Oligonucleotides were purified by HPLC and characterized by MALDI-TOF MS.

[Protected maleimide]-$^{5'}$dCAGATGTCAC. 90% in the crude; t$_R$=13.7 min; m/z 3309.8 [M–H]$^-$, M calcd. 3309.6.

[Protected maleimide]-$^{5'}$dTCTCCCAGCGTGCGCCAT. 97% in the crude; t$_R$=13.8 min; m/z 5708.4 [M–H]$^-$, M calcd. 5708.0.

[Protected maleimide]-$^{5'}$dCAGCAGCAGAGTCTTCATCAT. 86% in the crude; t$_R$=14.3 min: m/z 6684.5 [M–H]$^-$, M calcd. 6686.2.

[Protected maleimide]-$^{5'}$U$_{10}$. 75% in the crude; t$_R$=14.0 min; m/z 3297.7 [M–H]$^-$, M calcd. 3297.4.

Example 10

$^{5'}$maleimide-oligonucleotides

Microwave-Promoted Deprotection

A solution of [2-(1,7-dimethyl-3,5-dioxo-10-oxa-4-azatricyclo[5.2.1.0$^{2.6}$]dec-8-en-4-yl)-ethyl]-O—PO$_2^-$)-$^{5'}$-oligonucleotide in a 1:1 (v/v) MeOH/H$_2$O mixture (25 μM, 500-1000 μL) was introduced in a microwave vial and irradiated for 90 min at 90° C. The solvent was removed under vacuum (rotavap) and the resulting crude was dissolved in water and analyzed by HPLC (C18).

This procedure was used to prepare to following maleimide-oligonucleotides (in addition to maleimide-dT10, previously described): maleimide-$^{5'}$dCAGATGTCAC, maleimide-$^{5'}$dTCTCCCAGCGTGCGCCAT, maleimide-$^{5'}$dCAGCAGCAGAGTCTTCATCAT, and maleimide-$^{5'}$U$_{10}$ from the corresponding starting material.

Desprotection by Heating in Toluene

A solution of [2-(1,7-dimethyl-3,5-dioxo-10-oxa-4-aratricyclo[5.2.1.0$^{2.6}$]dec-8-en-4-yl)-ethyl]-O—PO$_2^-$)—$^{5'}$O-oligonucleotide was introduced in a vial and evaporated to dryness under vacuum (rotavap). The resulting residue was dried by coevaporation with toluene (2×), and toluene was added (the amount that would be required to obtain a 25 μM solution if the oligonucleotide were soluble in toluene). This mixture was heated for 3 h, after which time toluene was removed under reduced pressure. The resulting crude of maleimide-$^{5'}$oligonucleotide was dissolved in water and analyzed by HPLC (C18).

This procedure was used to prepare the following maleimide-oligonucleotides: maleimide-$^{5'}$dCAGATGTCAC, maleimide-$^{5'}$dTCTCCCAGCGTGCGCCAT, and maleimide-$^{5'}$dCAGCAGCAGAGTCTTCATCAT from the corresponding starting material.

Maleimide-oligonucleotides (aqueous solutions of the crudes) were analyzed by HPLC (C18). Characterization was accomplished by mass spectrometry (MALDI-TOF MS).

Maleimide-$^{5'}$dT$_{10}$: microwave-promoted retro Diels-Alder, yield: 97%; t$_R$=14.3 min; m/z 3180.5 [M–H]$^-$, M calc 3181.5.

Maleimide-$^{5'}$dCAGATGTCAC: microwave-promoted retro Diels-Alder, yield: 96%; retro Diels-Alder in toluene, yield: 99%; t$_R$=11.9 min; m/z 3213.7 [M–H]$^-$, M calcd. 3213.5.

Maleimide-$^{5'}$dTCTCCCAGCGTGCGCCAT: microwave-promoted retro Diels-Alder, yield: 96%; retro Diels-Alder in toluene, quantitative yield; t$_R$=13.8 min; m/z 5611.2 [M–H]$^-$, M calcd. 5611.9.

Maleimide-$^{5'}$dCAGCAGCAGAGTCTTCATCAT: microwave-promoted retro Diels-Alder, yield: 95%; retro Diels-Alder in toluene, yield: 94%; t$_R$=12.9 min; m/z 6589.8 [M–H]$^-$, M calcd. 6590.1.

Maleimide-$^{5'}$U$_{10}$: microwave-promoted retro Diels-Alder, yield: 92%; t$_R$=11.8 min; m/z 3201.6 [M–H]$^-$, M calcd. 3201.3.

The invention claimed is:

1. A compound of formula (I) substantially in exo configuration, or a salt thereof:

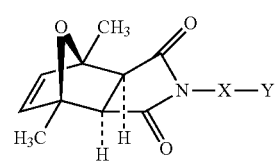

wherein:

X is a biradical selected from the group consisting of:

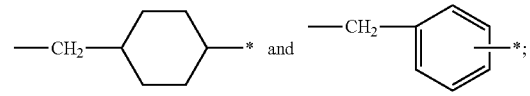

n is an integer ranging between 1 and 30;

* represents the position through which X binds to Y;

Y is a radical selected from the group consisting of:

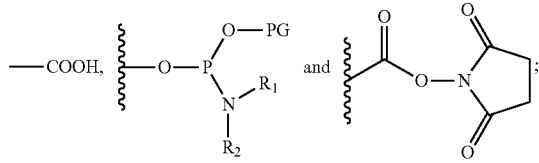

the wavy line representing the place through which Y binds to X;

PG is a phosphate protecting group; and $R_1$ and $R_2$ are the same or different to each other and are selected from the group consisting of a $C_1$-$C_{10}$ alkyl radical and a morpholine radical.

2. The compound of claim 1, wherein $R_1$ and $R_2$ are $C_1$-$C_{10}$ alkyl radicals.

3. The compound of claim 1, wherein PG is selected from the group consisting of —$CH_2CH_2CN$, methyl, 2-cyano-1,1-dimethylethyl, and p-nitrophenylethyl.

4. The compound of claim 1, wherein X is —$(CH_2)_n$—* or —$(CH_2CH_2O)_nCH_2CH_2$—*, and wherein * has the same meaning as in claim 1.

5. The compound of claim 1, wherein Y is —COOH or

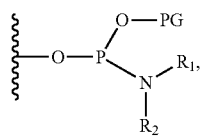

and wherein the wavy line, PG, $R_1$, and $R_2$ have the same meaning as in claim 1.

6. The compound of claim 1, being selected from the group consisting of compounds of formulae (Ia) and (Ib):

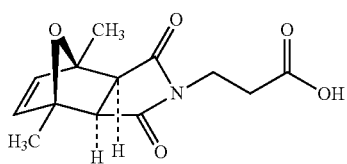

(Ia)

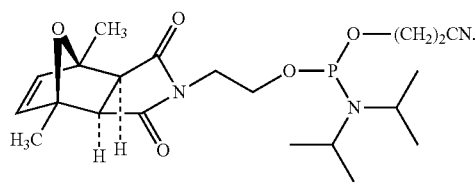

(Ib)

7. A process for preparing the compound of formula (I) defined in claim 1 wherein Y is —COOH, the process comprising the steps of:

(a) carrying out a Diels-Alder reaction between a compound of formula (II) and a compound of formula (III),

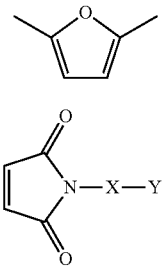

(II)

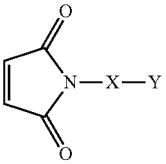

(III)

wherein X has the same meaning as in claim 1, and (b) carrying out a treatment of the compound obtained in step (a) with a nucleophilic base for isolating the compound of formula (I).

8. The process of claim 7, wherein step (b) comprises the following substeps ($b_1$) to ($b_4$):

($b_1$) contacting a compound obtained in step (a) with a nucleophilic base at room temperature;

($b_2$) removing the nucleophilic base to obtain a resulting medium;

($b_3$) acidifying the resulting medium to a pH equal to or less than 3 to form a resulting product; and ($b_4$) isolating the resulting product.

9. The process of claim 7, wherein the nucleophilic base is selected from ammonia, a primary amine, and a secondary amine.

10. A process for preparing a compound of formula (I) defined in claim 1, wherein Y is

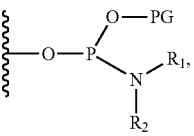

wherein the wavy line, PG, $R_1$, and $R_2$ have the same meaning as in claim 1, wherein the process comprises reacting a compound of formula (IV) with a compound of formula (V):

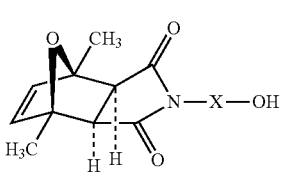

(IV)

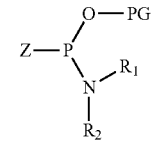

(V)

in an aprotic solvent and under anhydrous conditions, wherein Z is selected from halogen and diisopropylamine, and X has the same meaning as in claim 1.

11. A process for solid-phase preparation of the maleimide-oligonucleotide derivative of formula (VI), (VI)

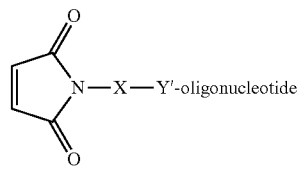

wherein X has the same meaning as in claim 1,
Y' is selected from

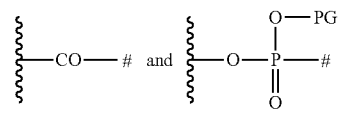

wherein the wavy line represents the place through which Y' binds to X, # represents the position through which Y' binds to the oligonucleotide, and PG has the same meaning as in claim 1;
the process comprising the following steps:
(a) coupling the compound of formula (I), defined in claim 1, to an oligonucleotide that is immobilized on a solid support, for obtaining the compound of formula (VII)

(VII)

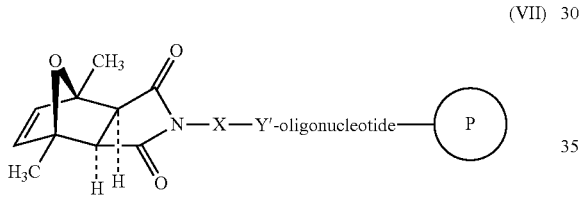

wherein P is the solid support,
(b) releasing the compound of formula (VII), resulting from step (a), from the solid support to give rise to the compound of formula (VIII); and (VIII)

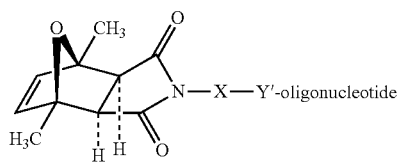

(c) subjecting the compound of formula (VIII) to a retro-Diels-Alder reaction, such that the maleimide-oligonucleotide derivative of formula (VI) is obtained.

12. The process of claim 11, wherein step (a) is carried out in the presence of pentafluorophenyl 4-nitrobenzenesulphonate and 1-hydroxybenzotriazole.

13. The process of claim 11, wherein step (b) is carried out in the presence of a nucleophilic base.

14. The process of claim 11, wherein step (c) is carried out with microwaves at a temperature in a range between 80-100° C.

15. The process of claim 11, wherein step (c) is carried out by adding an aromatic hydrocarbon ($C_6$-$C_8$) to the compound of formula (VIII) resulting from step (b), and heating at a temperature in a range of from 80 to 100° C.

16. The process of claim 15, wherein the aromatic hydrocarbon ($C_6$-$C_8$) is toluene.

17. The process of claim 11, wherein:
step (b) is carried out in the presence of a nucleophilic base; and
step (c) is carried out by adding an aromatic hydrocarbon ($C_6$-$C_8$) to the compound of formula (VIII) resulting from step b), and heating with microwaves at a temperature in a range of from 80 to 100° C.

18. A compound of formula (VII)

(VII)

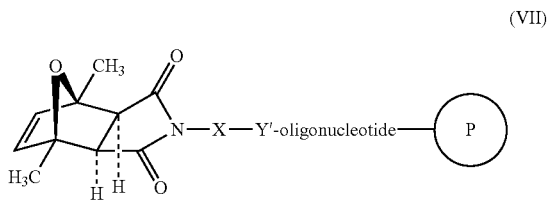

wherein
X is a biradical selected from the group consisting of:

—$(CH_2)_n$—*, —$(CH_2CH_2O)_n CH_2CH_2$—*,

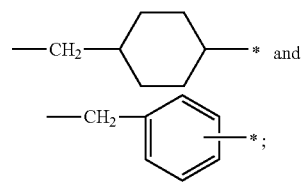

Y' is selected from

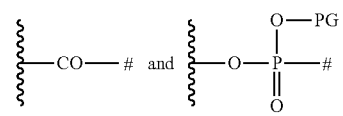

the wavy line represents the place by which Y' binds to X,
represents the place through which Y' binds to the oligonucleotide, and
P is a solid support.

19. A compound of formula (VIII)

(VIII)

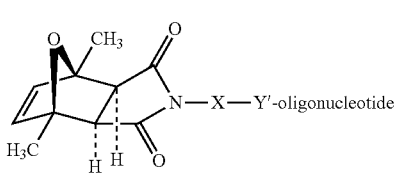

wherein
X is a biradical selected from the group consisting of:

—$(CH_2)_n$—*, —$(CH_2CH_2O)_n CH_2CH_2$—*,

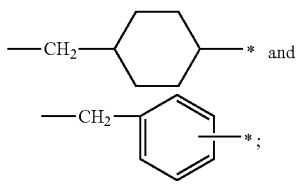
Y' is selected from
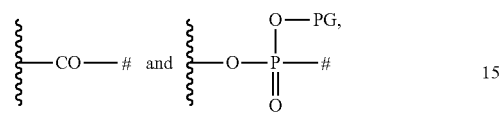
the wavy line represents the place by which Y' binds to X, and
represents the place through which Y' binds to the oligonucleotide.